United States Patent
Lehman

(10) Patent No.: US 10,500,421 B2
(45) Date of Patent: Dec. 10, 2019

(54) COMPOSITION FOR REDUCING THE TIME NEEDED TO DRY WET HAIR

(71) Applicant: Kenra Professional, LLC, Indianapolis, IN (US)

(72) Inventor: Thomas A Lehman, Indianapolis, IN (US)

(73) Assignee: KENRA PROFESSIONAL, LLC, Indianapolis, IN (US)

(*) Notice: Subject to any disclaimer, the term of this patent is extended or adjusted under 35 U.S.C. 154(b) by 0 days.

(21) Appl. No.: 14/069,662

(22) Filed: Nov. 1, 2013

(65) Prior Publication Data

US 2014/0137884 A1    May 22, 2014

Related U.S. Application Data

(60) Provisional application No. 61/721,241, filed on Nov. 1, 2012.

(51) Int. Cl.
*A61K 8/92* (2006.01)
*A61Q 5/12* (2006.01)
(Continued)

(52) U.S. Cl.
CPC .............. *A61Q 5/12* (2013.01); *A61K 8/31* (2013.01); *A61K 8/361* (2013.01); *A61K 8/39* (2013.01);
(Continued)

(58) Field of Classification Search
None
See application file for complete search history.

(56) References Cited

U.S. PATENT DOCUMENTS 4,894,224 A * 1/1990 Kuwata et al. ............... 514/781
2002/0102225 A1   8/2002 Hess et al.
(Continued)

FOREIGN PATENT DOCUMENTS

WO    2007051505 A1    5/2007
WO    2007051506 A1    5/2007
(Continued)

OTHER PUBLICATIONS

Gao T, Pereira A, Obukowho P. "A new multifunctional, shine-enhancing emollient: PPG-3 benzyl ether myristate". J Cosmet Sci. 2004;55 Suppl:S143-50.*
(Continued)

*Primary Examiner* — Nicole P Babson
(74) *Attorney, Agent, or Firm* — Benesch, Friedlander, Coplan & Aronoff LLP

(57) ABSTRACT

A composition and method for reducing the drying time of wet hair by about 20 to about 30 percent includes applying a silicone-free, non-aqueous composition comprising about 90 to about 96 percent by weight of a volatile hydrocarbon mixture comprising C13-C16 isoparaffin, C12-C14 isoparaffin; and C13-C15 alkane; about 2 to about 3 percent by weight of ppg-3 benzyl ether myristate; about 0.001 to about 0.01 percent by weight of a sodium laneth 40-maleate/styrene sulfonate copolymer; and about 0.01 to about 0.5 percent by weight of an emollient mixture comprising isostearic acid, sorbitan oleate, cocoyl hydrolyzed keratin and heat to wet hair, thereby removing from about 85% to about 100% of water added to the hair during washing.

11 Claims, 1 Drawing Sheet

(51) Int. Cl.
*A61K 8/81* (2006.01)
*A61K 8/31* (2006.01)
*A61K 8/36* (2006.01)
*A61K 8/39* (2006.01)
*A61K 8/49* (2006.01)
*A61K 8/65* (2006.01)
*A61Q 5/06* (2006.01)

(52) U.S. Cl.
CPC .............. *A61K 8/4973* (2013.01); *A61K 8/65* (2013.01); *A61K 8/8117* (2013.01); *A61K 8/8188* (2013.01); *A61Q 5/06* (2013.01); *A61K 2800/31* (2013.01); *A61K 2800/34* (2013.01)

(56) References Cited

U.S. PATENT DOCUMENTS

| | | | |
|---|---|---|---|
| 2007/0243143 | A1 | 10/2007 | Patil et al. |
| 2007/0248550 | A1 | 10/2007 | Patel et al. |
| 2007/0269389 | A1 | 11/2007 | Fuscelli et al. |
| 2009/0123398 | A1* | 5/2009 | Laba et al. ................. 424/59 |
| 2009/0165812 | A1 | 7/2009 | Resnick et al. |
| 2010/0012142 | A1 | 1/2010 | Presti |
| 2010/0028272 | A1 | 2/2010 | Knappe et al. |
| 2010/0092408 | A1 | 4/2010 | Breyfogle |
| 2011/0265810 | A1* | 11/2011 | Pelusi ................. A45D 7/06 132/206 |
| 2012/0076842 | A1 | 3/2012 | Fournial et al. |
| 2012/0093755 | A1 | 4/2012 | Humphreys et al. |
| 2012/0183485 | A1 | 7/2012 | Belluscio et al. |
| 2012/0276035 | A1 | 11/2012 | Lehman, Jr. |

FOREIGN PATENT DOCUMENTS

| | | | |
|---|---|---|---|
| WO | 2009055489 | A1 | 4/2009 |
| WO | 2010068661 | A1 | 6/2010 |
| WO | 20110077083 | A1 | 6/2011 |
| WO | 20120064482 | A1 | 3/2012 |

OTHER PUBLICATIONS

Tri-K Industries. "Hair Care: Elegant hair solutions" <http://tri-k.com/sites/default/files/WWHairInsert.pdf> available Apr. 10, 2009, accessed Jan. 21, 2015).*
Cosmetics Info "Squalene" <http://cosmeticsinfo.org/ingredient/squalene>available Dec. 27, 2007, accessed Jan. 22, 2015.*
Sigma-Aldrich, "Decamethylcyclopentasiloxane" < http://www.sigmaaldrich.com/catalog/product/aldrich/444278?lang=en&region=US>, accessed Aug. 6, 2015.*
Sigma-Aldrich, "Squalane" < http://www.sigmaaldrich.com/catalog/product/ aldrich/234311?lang=en&region=US#>, accessed Aug. 6, 2015.*
SiClone SR-5 Technical data sheet. < http://www.lipocol.com/applications/lipocolombia/archivos/114_INFORMACIN_TCNICA.pdf> accessed Aug. 5, 2014.*
SiClone SR-5 Technical Data Sheet <http://www.lipocol.com/applications/lipocolombia/archivos/114_INFORMACIN_TCNICA.pdf>, available May 2009; accessed Aug. 5, 2015 (Year: 2009).*
International Search Report and Written Opinion, dated Feb. 13, 2014, PCT/US2013/067987, pp. 1-13.
Larsen, et al., Siloxanes-consumption, toxicity and alternatives, The Danish Environmental Protection Agency, 2005, Environmental Project No. 1031, pp. 5, 7-11, 19-21 and 32-34.
Final Office Action from U.S. Appl. No. 13/097,773, dated Oct. 11, 2013, pp. 1-16.
International Search Report and Written Opinion, dated Feb. 24, 2014, PCT/US2013/067993, pp. 1-12.
Amazon.com: "Kenra Platinum Blow-Dry Spray" XP-002755194 retrieved Jul. 3, 2016, 5 pages.
"Abstracts of Papers Published in the Journal of Cosmetic Science" XP-002755196, International Journal of Cosmetic Science, vol. 27, 2005, pp. 135-141.
"MiruStyle X-HP" XP-002755197, Croda, DC128, Jun. 2009, pp. 1-16.
"Ethnic Hair Care Ingredients" XP-002755198, The Free Library, 2003, 20 pages.
European Search report regarding related application EP 13 85 1392 dated Apr. 29, 2016.

* cited by examiner

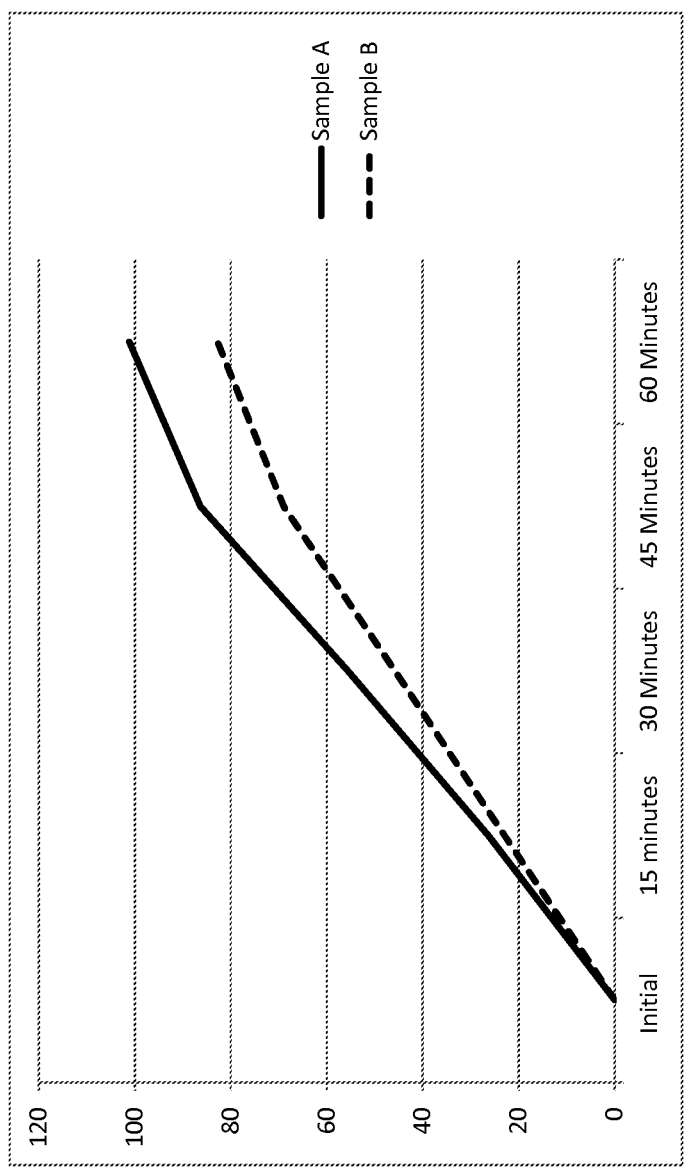

COMPOSITION FOR REDUCING THE TIME NEEDED TO DRY WET HAIR

RELATED APPLICATIONS

This application claims priority to U.S. Provisional Patent Application No. 61/721,241 filed on Nov. 1, 2012, entitled Composition for Reducing the Time Needed to Dry Wet Hair.

FIELD OF THE INVENTION

The present disclosure relates to silicone-free compositions for use in hair that are capable of reducing the time needed to blow dry wet hair. In addition, the compositions may include those that thermally protect, reduce frizz, and/or soften hair and leave-in treatments that can be applied to hair as a mist.

BACKGROUND

In order to create hairstyles, treatment compositions in the form of setting lotions, aerosol and non-aerosol sprays, setting foams, and gels are used. It would be desirable to provide users with a composition that also decreased drying time for hair, especially for those users with long or thick hair. Many attempts have been made to reduce the drying time of hair, but the known compositions form coatings on hair, making it less water repellent and therefore less efficient in decreasing time to dry hair; also the coatings are less resistant towards washing with shampoo and gets degraded more rapidly. It would be desirable to develop a formulation that could be applied after the hair is washed and would also not leave a residue on the clean hair.

SUMMARY

One embodiment includes a composition and method for reducing the drying time of wet hair by about 20 to about 30 percent by applying a silicone-free composition comprising about 90 to about 96 percent by weight of a volatile hydrocarbon mixture comprising C13-C16 isoparaffin, C12-C14 isoparaffin; and C13-C15 alkane; about 2 to about 3 percent by weight of ppg-3 benzyl ether myristate; about 0.001 to about 0.01 percent by weight of a sodium laneth 40-maleate/styrene sulfonate copolymer; and about 0.01 to about 0.5 percent by weight of an emollient mixture comprising isostearic acid, sorbitan oleate, cocoyl hydrolyzed keratin and heat to wet hair, thereby removing from about 85% to about 100% of added water.

In another embodiment, the silicone-free composition may also include an additive selected from one or more of a fragrance, keratin, emulsifiers, or essential oils such as safflower oil, argan oil, or jojoba seed oil and may have a density of about 0.84 g/ml.

DESCRIPTION OF THE DRAWINGS

FIG. 1 is a graphical representation of the percent of water lost in Samples A and B as a function of time.

DETAILED DESCRIPTION

The silicone free composition for reducing the drying time of wet hair includes a volatile hydrocarbon mixture of straight and branched chain paraffin compounds, an emollient, and a thermal protectant. The composition may also include one or more hair conditioning agents, such as safflower oil, jojoba oil, or keratin, emulsifiers, and fragrances. The composition can be applied with a spray bottle or other apparatus capable of spraying, misting, or otherwise applying in very small droplets, the composition onto a user's hair. The composition may also be applied as a gel, a foam, or in other suitable forms.

The composition may include small amounts of water, less than about one percent, but is nonaqueous. For the purposes of this disclosure, compositions that include less than about one percent water are considered to be nonaqueous. The composition may be preferably less dense than water, with a preferred density of between 0.7 g/ml and 0.98 g/ml, preferably about 0.84 g/ml. The composition may also be preferably colorless.

The composition includes a silicone-free volatile mixture of straight and branched chain paraffin compounds. As used herein, the term "volatile" when employed in relation to a hydrocarbon compounds includes compounds that exhibit a vapor pressure of more than about 0.2 mm Hg at 25° C. at one atmosphere of pressure or have a boiling point at one atmosphere of less than the boiling point of water, i.e. less than about 100° C.

The silicone-free volatile mixture may include at least one non-volatile hydrocarbon compound and at least one, but preferably a combination of at least two, volatile hydrocarbon compounds. One example of a suitable volatile mixture includes C13-C16 isoparaffin, C12-C14 isoparaffin, and C13-C15 alkane, commercially available from Presperse under the trade name SiClone SR-5. Another suitable mixture is JEESILC SR-5, commercially available from JEE International Corp. In one embodiment, the composition includes from about 90 percent to about 97 percent by weight of the silicone-free volatile mixture, and in another embodiment from about 93 to about 95 percent by weight of the final composition. All weight percentages disclosed herein are based upon the weight of the final composition, unless otherwise stated.

The composition also includes at least one emollient. Broadly, cosmetically acceptable emollients may be used in the composition. In one embodiment, ppg-3 benzyl ether myristate, commercially available from Croda under tradename Crodamol STS, may be used. Specifically, the composition may include from about 2 to about 4 percent by weight of a the ppg-3 benzyl ether mysistate, and preferably from about 3 percent by weight of the final composition.

The composition may also optionally include other cosmetically acceptable additives, such as thermal protective agents (a.k.a. thermoprotective agent), hair conditioning agents, fragrance, and essential oils. Suitable fragrances and hair conditioning agents may include, but are not limited to, agar, argan, balsam, basil, bay, bergamot, cardamom seed, cedarwood, cranberry, frankincense, geranium, grapefruit, jasmine, jojoba seed, lavender, lemon, litsea cubeba, orange, orris, parsley, patchouli, rose, rosemary, rosewood, safflower, sassafras, savory oil, star anise, tangerine oils, cocoyl hydrolyzed keratin, and combinations thereof.

In one embodiment, the composition may optionally include one or more of (1) from about 2.0 to about 3.0 percent by weight, preferably about 2.25 percent by weight safflower oil, (2) from about 0.01 to about 1.0 percent by weight, preferably about 0.1 to about 0.3 percent by weight, jojoba seed oil, and (3) from about 0.1 to about 2.0 percent by weight, preferably 0.2 to about 0.5 percent by weight, of a fragrance additive, such as Mango Melody.

The composition may also include from about 0.001 to about 1 percent by weight of at least one thermal protective agent, such as a sodium laneth 40 maleate/styrene sulfonate copolymer, or other suitable thermal protector. One commercially available thermal protective agent is Mirustyle X-HP from Croda. Another example is commercially available as Mirustyle X-HV from Croda.

The composition may also include an emollient mixture, such as a combination of isostearic acid, sorbitan oleate, and cocoyl hydrolyzed keratin. One example of such as combination is Protolan KT from Tri-K, Inc. In one embodiment, the composition includes from about 0.01 to about 0.5 percent by weight of the emollient mixture.

EXAMPLE

The composition is illustrated by the following non-limiting example. The composition is prepared by mixing the following ingredients according to the amounts in Table I below:

TABLE I

| Component | Weight % |
|---|---|
| C13-C16 Isoparaffin, C12-C14 Isoparaffin, C13-C15 Alkane[1] | 94.14 |
| PPG-3 Benzyl Ether Myristate[2] | 3.00 |
| Sodium Laneth 40 Maleate/Styrene Sulfonate Copolymer[3] | 0.001 |
| Safflower Oil[4] | 2.25 |
| Jojoba Seed Oil[4] | 0.10 |
| Fragrance Mango Melody[5] | 0.50 |
| Cocoyl Hydrolyzed, Isostearic Acid Keratin, Sorbitan Oleate[6] | 0.01 |

[1]Available from Presperse under the trade name SiClone SR-5
[2]Available from Croda under the trade name Crodamol STS
[3]Available from Croda under the trade name Mirustyle XHP
[4]Available from Columbus Foods
[5]Available from Belmay Fragrances
[6]Available from TRI-K, Inc. under the trade name Protolan KT In the example provided in Table I, batches, in either 1 or 2 pound quantities, of the composition were prepared by individually adding the volatile paraffin mixture to a Caframo lab mixer having three blades with a total diameter of 2-2.5 inches. The mixture was then blended. Under a moderate mixing speed, the remaining compounds were added to the composition. The composition was then mixed for about 30 minutes until fully blended to form the final treatment composition. In other embodiments, it is contemplated that one, all, or none of the emollients and conditioning agents may be included in the final treatment composition. It is also noted that the overall final treatment composition may include as much as, but no more than 1.0% water, by weight.

The final treatment composition prepared according to Table I was found to be capable of reducing the drying time of wet hair. For purposes of this disclosure, to "dry" wet hair means to remove at least 85% of added water weight. To be capable of reducing the drying time of wet hair, the composition decreases the time, in minutes, needed to evaporate from 85% to 100% of the added water weight on a swatch of human hair when subjected to a pre-selected amount of heat, as compared to a similar, but untreated, swatch of hair subjected to the same amount of heat.

The composition prepared according to Table I was found to be capable of reducing the drying time of wet hair by up to 25%, compared to untreated wet hair. In order to compare the time needed to blow dry wet hair, the dry weight of hair swatches was measured. The swatches, Samples A and B, were submerged in water and uniformly towel blotted to remove some amount of water. The towel-dried wet swatches was then weighed. Five pump sprays (0.45-0.5 g total) of the composition made according to the specifications of Table I were applied to Sample A using a spray bottle with a pump dimension of 37 MS and a 180 microliter dosage. Sample B was not treated with the composition The samples were placed under a conventional hood drier set on perm, 120° F. (±2° F.), and allowed to dry for 15 minutes. All samples were then weighed. This procedure was repeated an additional three times, for a total of 60 minutes of time under the drier hood for all of the samples.

The weight of water lost during the testing procedure was then calculated for Samples A and B by comparing the weight of the dry swatch with the weight of the wetted swatches at different drying intervals. The weight percent of added water lost over the course of an hour is set forth in FIG. 1 and Table II below.

TABLE II

| | % Added Water Removed | | | | |
|---|---|---|---|---|---|
| | Initial | 15 Min | 30 min | 45 min | 60 min |
| A | 0.0 | 26.34 | 55.58 | 86.30 | 98.61 |
| B | 0.0 | 22.98 | 45.77 | 68.95 | 82.73 |

As demonstrated above, sample A prepared according to the present disclosure decreased the time needed to dry wet hair by at least 25%.

In use, the composition may be applied to wet hair, i.e. hair that has had water added to it, for example, during washing. After the hair is towel dried, the composition is lightly sprayed on the hair in sections and combed through. Once applied, heat is then added to the hair by a blow drier or other suitable methods. In one embodiment, heat is applied to sections of the hair as it is pulled away from the scalp with a brush or a user's hand. A round brush may be used to create volume during the drying process. In one embodiment, the time needed to dry a user's hair is decreased by about 20 to about 30%, however the time needed to dry the user's wet hair may be decreased by as much as 50%.

While the composition and methods herein have been described with a number of embodiments, the scope is not intended to be limited by the specific embodiments. Modifications and variations from the described embodiments exist. Although numerous ingredients suitable for formulating the hair styling composition have been listed, the list is by no means exhaustive. It is, of course, not possible to describe every conceivable combination of components or methodologies for purposes of describing the systems, methods, devices, and so on, described herein. Additional advantages and modifications will readily appear to those skilled in the art. Therefore, the invention is not limited to the specific details, the representative revascularization catheter systems, and illustrative examples shown and described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

The invention claimed is:

1. A composition comprising:
   at least about 90 to about 96 percent by weight of a volatile hydrocarbon mixture consisting of C13-C16 isoparaffin, C12-C14 isoparaffin; and C13-C15 alkane, wherein the volatile hydrocarbon mixture exhibits a vapor pressure of more than about 0.2 mm Hg at 25°

C at one atmosphere of pressure or has a boiling point at one atmosphere of less than about 100° C.;

about 2 to about 3 percent by weight of ppg-3 benzyl ether myristate;

about 0.001 to about 0.01 percent by weight of a sodium laneth 40-maleate/styrene sulfonate copolymer; and about 0.01 to about 0.5 percent by weight of an emollient mixture comprising isostearic acid, sorbitan oleate, cocoyl hydrolyzed keratin, and less than about 1 percent by weight of water; wherein the composition is a silicone-free, non-aqueous, sprayable composition configured to reduce the drying time of wet hair and has a density of between about 0.7 g/ml to about 0.98 g/ml.

2. The composition of claim 1, wherein the composition further comprises an additive selected from one or more of a fragrance or an essential oil.

3. The composition of claim 1, wherein the composition has a density of about 0.84 g/ml.

4. The composition of claim 1, wherein the composition further comprises at least one cosmetically acceptable additive.

5. The composition of claim 4, further comprising a second cosmetically acceptable additive.

6. The composition of claim 5, wherein the second cosmetically acceptable additive comprises a fragrance.

7. The composition of claim 5, wherein the second cosmetically acceptable additive comprises an essential oil.

8. The composition of claim 5, wherein the second cosmetically acceptable additive comprises a hair conditioning agent.

9. The composition of claim 1, wherein the volatile hydrocarbon mixture consists of about 55 percent by weight of C13- C16 isoparaffin, about 35 percent by weight of C12-C14 isoparaffin, and about 10 percent by weight of C13- C15 alkane.

10. A method for reducing the drying time of wet hair, comprising the steps of:

applying added water to human hair to obtain wet hair;

supplying a silicone-free composition comprising about 90 to about 96 percent by weight of a volatile hydrocarbon mixture consisting of C13- C16isoparaffin, C12- C14isoparaffin; and C13- C15alkane, wherein the volatile hydrocarbon exhibits a vapor pressure of more than 0.2 mm Hg at 25° C. at one atmosphere of pressure or has a boiling point at one atmosphere of less than about 100° C.;

about 2 to about 3 percent by weight of ppg-3 benzyl ether myristate;

about 0.001 to about 0.01 percent by weight of a sodium laneth 40-maleate/styrene sulfonate copolymer; and about 0.01 to about 0.5 percent by weight of an emollient mixture comprising isostearic acid, sorbitan oleate, cocoyl hydrolyzed keratin, and less than about 1percent by weight of water; wherein the composition is a silicone-free, non-aqueous, sprayable composition configured to reduce the drying time of wet hair and has a density of between about 0.7 g/ml to about 0.98 g/ml;

applying the silicone-free composition to the wet hair;

applying heat to the wet hair;

removing from about 85% to about 100% of the added water; and wherein the silicone-free composition is capable of reducing a drying time of wet hair by about 20 to about 30 percent compared to the drying time of wet hair that was not treated with the silicone-free composition.

11. The method of claim 10, wherein the silicone-free composition further comprises an additive selected from one or more of fragrance or an essential oil.

* * * * *